| (12) | United States Patent<br>Martin | (10) Patent No.: US 8,481,949 B2<br>(45) Date of Patent: Jul. 9, 2013 |
|---|---|---|

(54) APPARATUS AND METHODS FOR COOLING POSITRON EMISSION TOMOGRAPHY SCANNER DETECTOR CRYSTALS

(75) Inventor: Matthew Eric Martin, Powell, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 39 days.

(21) Appl. No.: 13/295,250

(22) Filed: Nov. 14, 2011

(65) Prior Publication Data

US 2013/0119259 A1    May 16, 2013

(51) Int. Cl.
*G01T 1/164*    (2006.01)
(52) U.S. Cl.
USPC .................................................. 250/363.03
(58) Field of Classification Search
USPC ............... 250/363.01–363.1, 370.01–370.15, 250/362; 378/98.8
See application file for complete search history.

(56) References Cited

U.S. PATENT DOCUMENTS

2005/0167599 A1*  8/2005  Schlyer et al. ........... 250/363.03
2010/0188082 A1*  7/2010  Morich et al. ................ 324/307

* cited by examiner

*Primary Examiner* — Kiho Kim
(74) *Attorney, Agent, or Firm* — Peter Kendall

(57) ABSTRACT

Detector crystals in a positron emission tomography (PET) apparatus gantry are cooled by directing cooling gas flow into a cooling duct bounded by the crystals and a cover defining the patient scanning field within the gantry. The cooling gas cools the crystals. Cooling gas may also be directed radially outwardly from the cooling duct into spatial gaps defined between detector enclosures that include the crystals, further isolating heat generated by other components within gantry from the detector crystals. Cooling gas is provided by a cooling system that may be incorporated within the gantry, external the gantry or a combination of both. Cooling gas can be provided by directing air within the gantry in contact with internal gantry cooling tubes and routing cooled air directly into the cooling duct with a powered fan.

17 Claims, 7 Drawing Sheets

APPARATUS AND METHODS FOR COOLING POSITRON EMISSION TOMOGRAPHY SCANNER DETECTOR CRYSTALS

BACKGROUND OF THE DISCLOSURE

1. Field of the Invention

The invention relates to positron emission tomography (PET) scanners used to image areas of interest in patients, and particularly apparatus and methods for cooling PET scanner detector scintillation crystals, so that they are maintained at a stabilized temperature selected for desired detector performance.

2. Description of the Prior Art

PET scanners image areas of interest in patients who have ingested radioactive imaging solutions. The scanner utilizes an array of scintillation crystals in a generally annular scanner gantry to detect radioactive particle emissions from the patient; and then correlates those emissions with patient tissue structure. One known scintillation crystal material is lutetinium oxy-orthosilicate (LSO). In PET scanner operation, a radioactive particle emitted from the patient striking a detector crystal within a detector element causes a light emission. That light emission is in turn detected by a photomultiplier tube (PMT), charge coupled device or the like. The PMT in cooperation with a detector electronics assembly (DEA) converts the scintillation crystal's detected light emission to an electrical signal that is used by scanner to generate an image of patient tissue in the area of interest.

Light output of scanner scintillation crystals can be temperature dependent. As shown in FIG. 1, a lutetinium oxy-orthosilicate (LSO) crystal reduces effective light output (hence detector sensitivity) unless stabilized detector crystal temperature is maintained below 300° Kelvin (81° F. or 27° C.). Known PET scanners passively maintain detector crystal temperature. Components within the PET scanner gantry, for example the DEAs, generate and emit heat during their operation that is trapped within enclosed, sealed gantries. Ambient air ventilation is not commonly utilized in PET scanner gantries. Known PET scanners utilize water-cooled heat exchanger cooling rings in the sealed gantry structure to absorb and transfer heat away from the scanner. Cooling rings incorporated in the gantry structure rely primarily on convective heat transfer, assisted somewhat by forced exhaust fans incorporated within the DEA structures. Detector crystals are indirectly cooled by attempting to maintain the overall operating temperature within the gantry sufficiently low to meet the crystal operational temperature needs. However, localized temperature zones within the scanner gantry are not controlled with sufficient precision to assure constant operational temperature needed to maximize scintillation crystal detector sensitivity. Thus, the cooling ring heat transfer system is operated at a higher heat transfer output level than necessary to cool all gantry components generally, without assurance that the indirectly cooled detector crystals are being maintained at their optimum stabilized temperature threshold.

SUMMARY OF THE INVENTION

Accordingly, an object of the invention is to maintain desired stabilized temperature of PET scanner detector scintillation crystals during scanner operation, so that detector sensitivity is increased and stabilized.

Another object of the present invention is to reduce cooling energy in PET scanner gantries that is needed to maintain desired stabilized temperature of detector scintillation crystals.

An additional object of the present invention is maintain desired stabilized temperature of PET scanner detector scintillation crystals during scanner operation in a manner that does not reduce scanner sensitivity.

These and other objects are achieved in accordance with the present invention by directly cooling detector crystals in a positron emission tomography (PET) apparatus gantry. The detector crystals are cooled by directing cooling gas flow into a cooling duct bounded by the crystals and a cover defining the patient scanning field within the gantry. The cooling gas cools the crystals. Cooling gas may also be directed radially outwardly from the cooling duct into spatial gaps defined between detector enclosures that include the crystals, further isolating heat generated by other components within gantry from the detector crystals. Cooling gas is provided by a cooling system that may be incorporated within the gantry, external the gantry or a combination of both. Cooling gas can be provided by directing air within the gantry in contact with internal gantry cooling tubes and forcing/routing the routing cooled air directly into the cooling duct with a powered fan.

One aspect of the present invention features a positron emission tomography (PET) scanner apparatus comprising a gantry having therein a cover defining a patient scanning field within the gantry. The gantry includes a plurality of detector enclosures, each having a detector crystal facing the patient scanning field. A cooling duct is formed in spatial volume bounded by the cover and the detector crystals. A cooling system is coupled to the cooling duct, and provides a source of forced cooling gas flow, such as cooled air, into the cooling duct.

Another aspect of the present invention features a positron emission tomography (PET) scanner apparatus comprising an annular gantry having therein a cover defining a patient scanning field within an inner radial circumference of the gantry. The gantry also has an array of a plurality of detector enclosures, each respective detector enclosure having a detector crystal facing the patient scanning field. The gantry includes a pair of opposed spaced axial shields axially bounding the detector enclosure array. An annular cooling duct bounded by the cover, the pair of axial shields and the detector crystals forms a spatial volume that is cooled by a cooling system that is directly coupled to the cooling duct. The cooling system provides a source of forced cooling gas flow into the cooling duct in order to cool the crystals.

Yet another aspect of the present invention features a method for cooling PET scanner detector crystals, the scanner having a gantry including a cover defining a patient scanning field within the gantry; a plurality of detector enclosures, each having a detector crystal facing the patient scanning field; and a cooling duct bounded by the cover and the detector crystals. The detector crystal cooling method is performed by coupling a cooling system capable of generating a forced cooling gas flow to the cooling duct and directing forced cooling gas flow into the cooling duct with the cooling system. In the case of LSO detector crystals an additional feature and aspect of this cooling method is maintaining crystal temperature below 81 degrees Fahrenheit (27° C. or 300° K), for higher light output (hence, greater detector sensitivity) than LSO crystals operated above that temperature.

The objects and features of the present invention may be applied jointly or severally in any combination or sub combination by those skilled in the art."

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

After considering the following description, those skilled in the art will clearly realize that the teachings of the present invention can be readily utilized in positron emission tomography (PET) scanner apparatus to cool detector crystals. Further, cooling the detector crystals is achieved without adding materials between the detector crystal face and the patient—thus not sacrificing scanner sensitivity. In the case of LSO material detector crystals, maintaining an operating temperature below 81° F. (27° C.) enhances their light output, and hence detector sensitivity.

Figure 1:
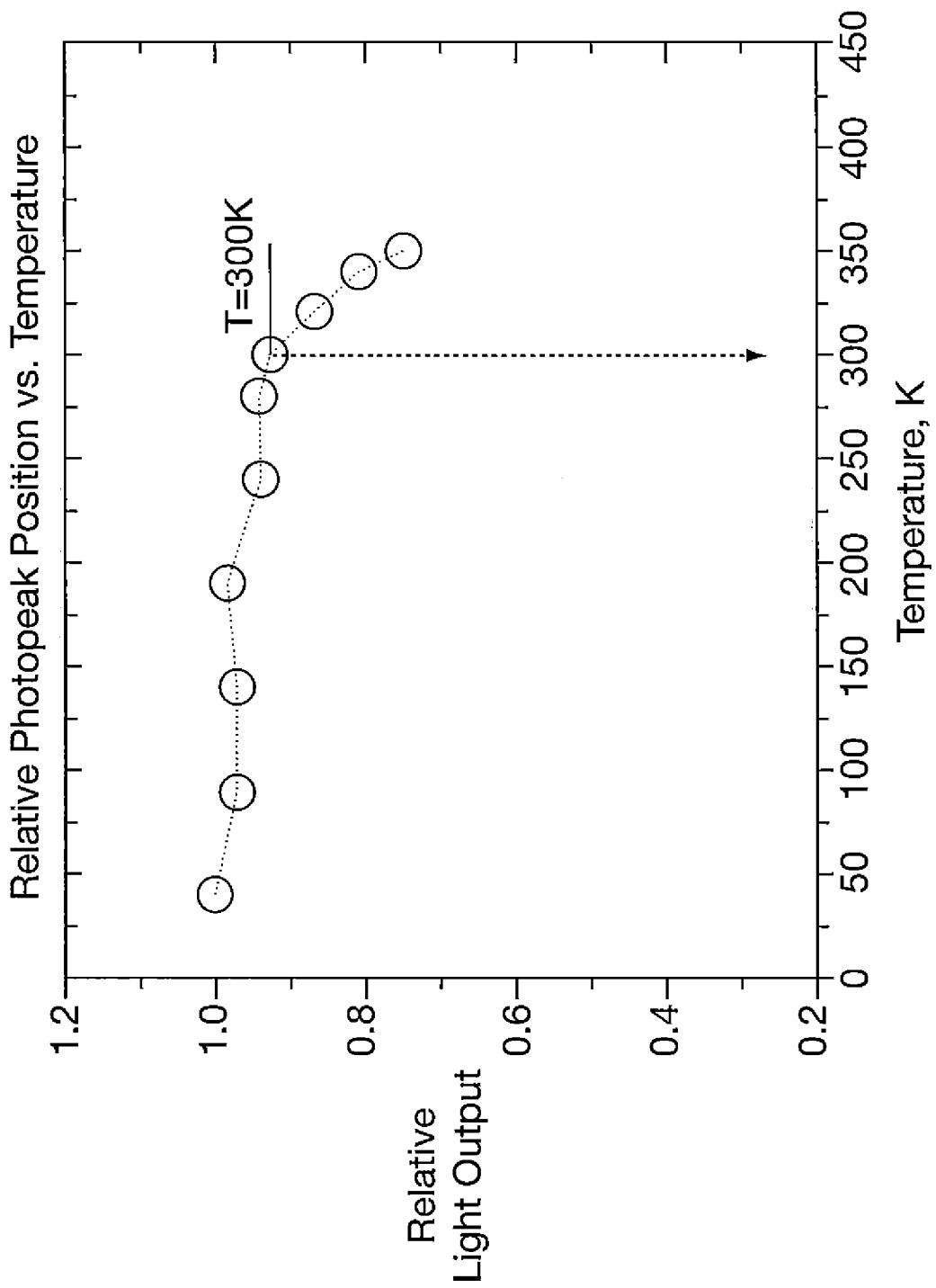
FIG. 1 is a graph of relative light output as a function temperature in an LSO crystal.
Figure 2:
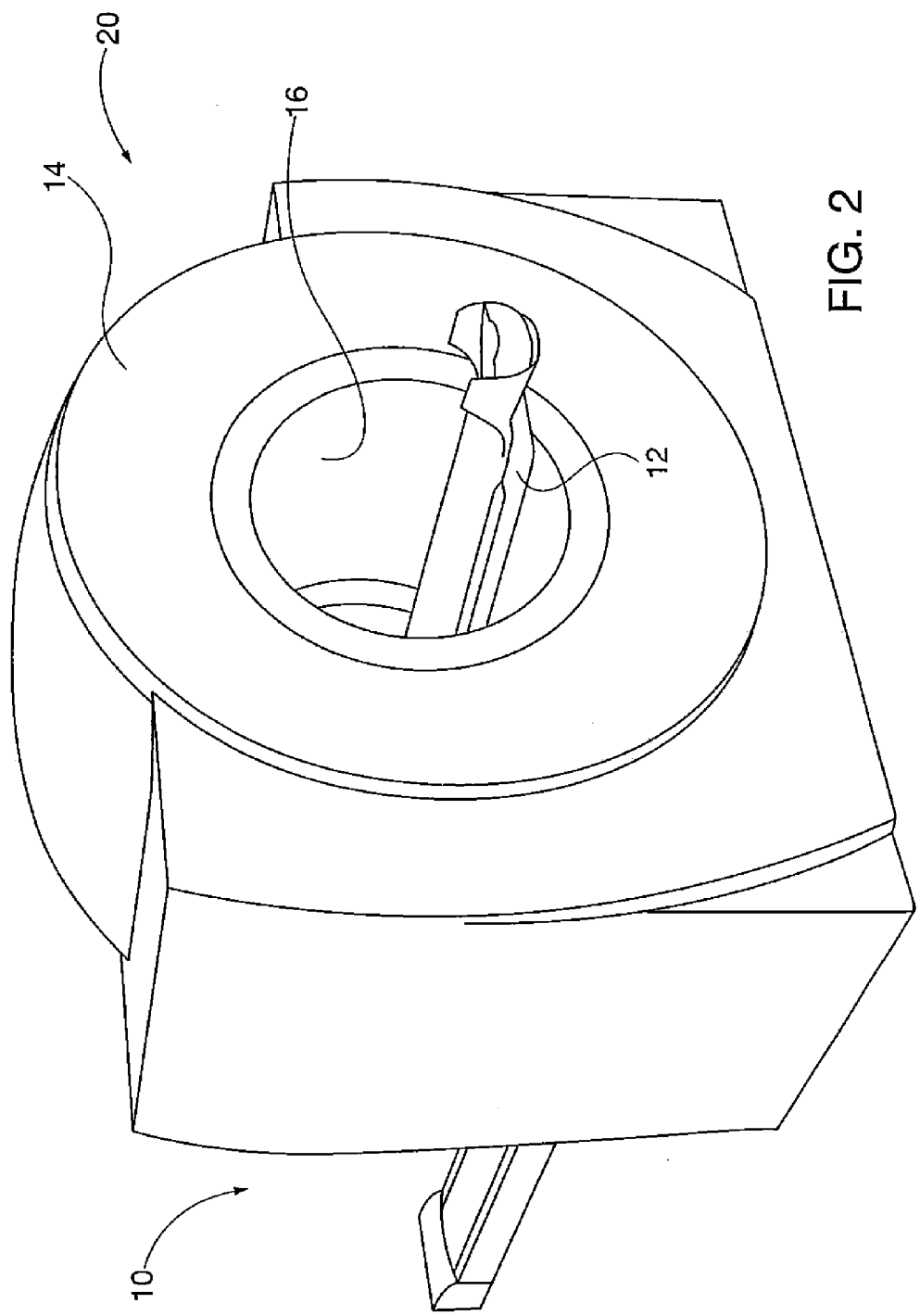
FIG. 2 is a perspective view of a positron emission tomography (PET) scanner imaging apparatus directed to an embodiment of the present invention.

FIGS. 2-7 show embodiments of the detector crystal cooling apparatus and methods of the present invention. FIG. 2 shows a PET scanner 10 having a patient bed 12 that translates relative to a scanning field. General structure and operation of the scanning components used to form an image representative of the scanned area of interest in the patient is known to those skilled in the art, and for brevity is not explained in further detail herein. The scanner 10 also includes a cover structure including an axial exterior cover 14 and a patient scanning field cover 16, both of which are generally annular-shaped and supported by the gantry 20.

Figure 3:
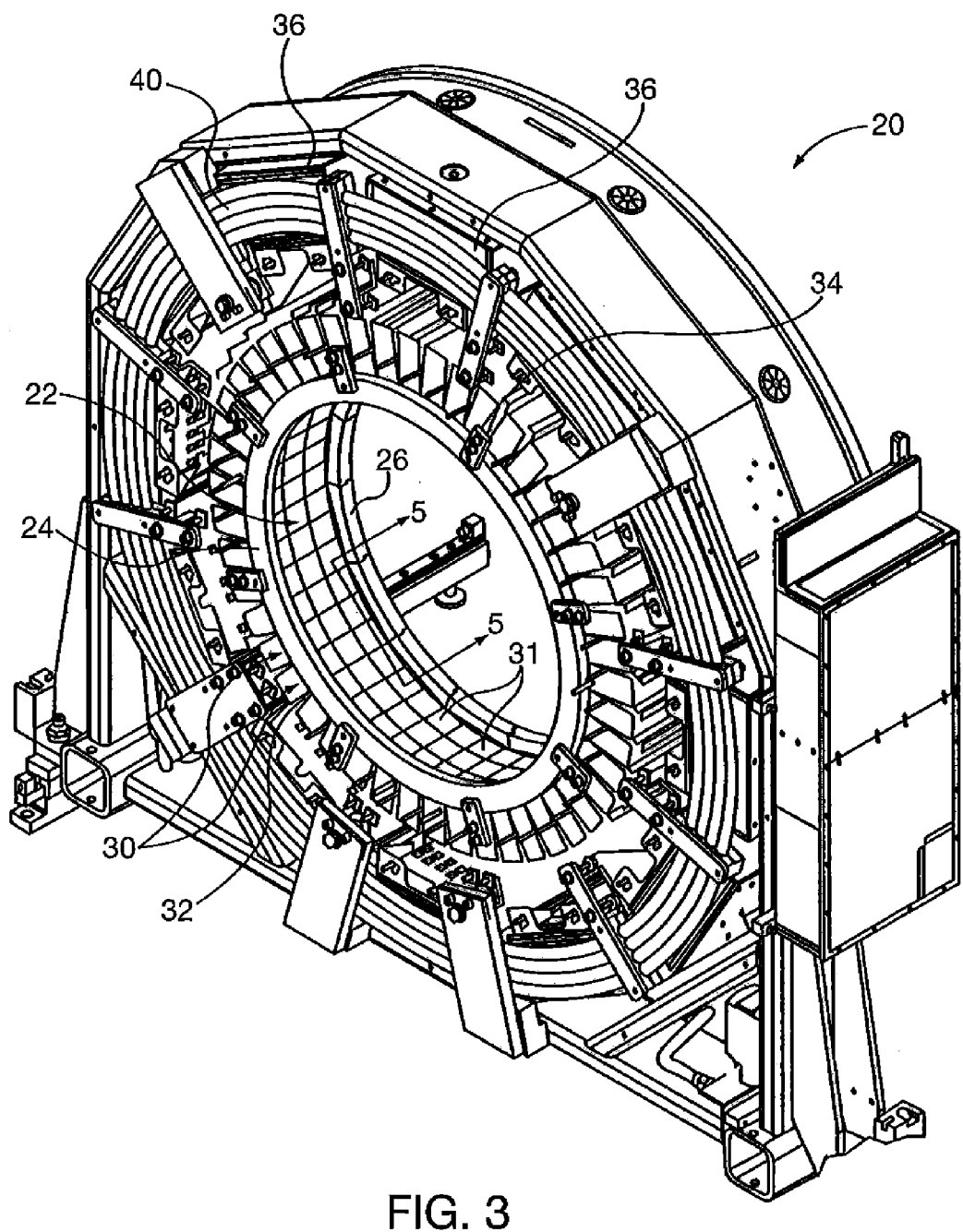
FIG. 3 is a perspective view of the embodiment of FIG. 1 without external covers and cooling ducts.
Figure 5:
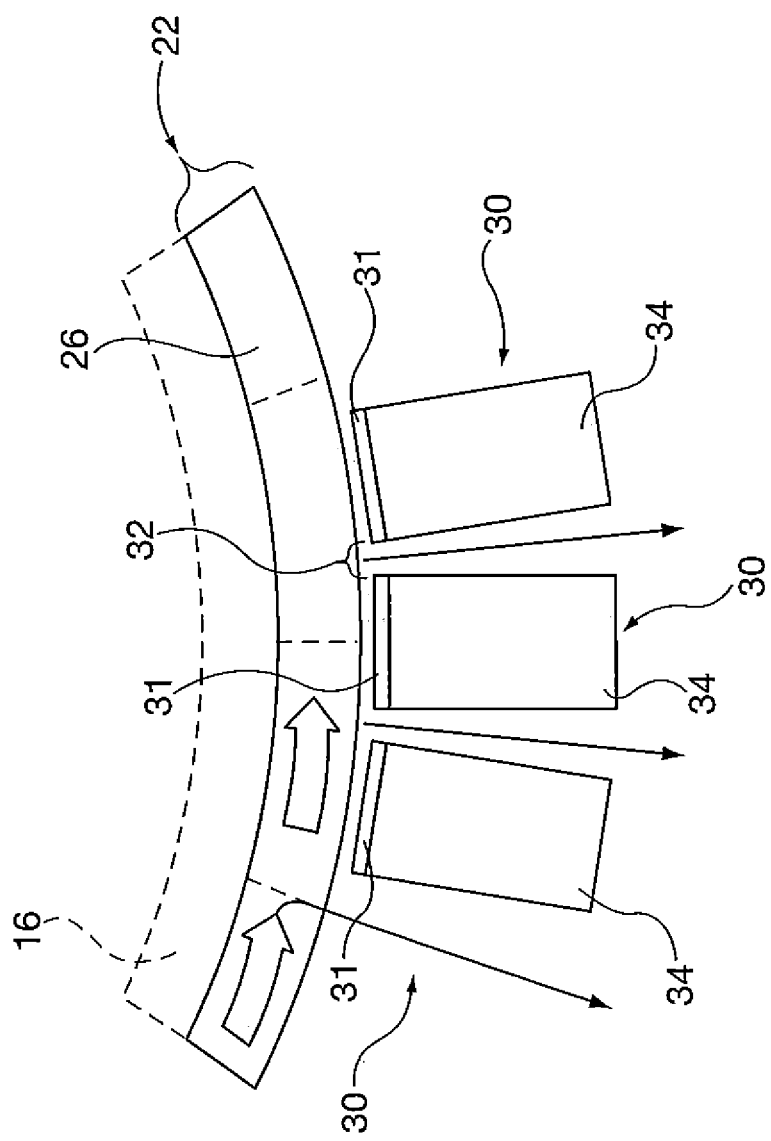
FIG. 5 is a detailed elevational schematic view of the embodiment of FIG. 4, showing cooling gas circumferential flow across detector crystals and radial flow through gaps formed between detector enclosures within the detector array.

Referring to FIGS. 3 and 5, gantry 20 has an annular shaped transaxial spatial volume 22 that is bounded by axial end shields 24, 26, the patient scanning field cover 16 and the circumferential (radial and axial) array of a plurality of detectors 30. Each detector 30 has a detector crystal 31 that may comprise lutetinium oxy-orthosilicate (LSO), or other suitable known material. Detectors 30 have spatial gaps 32 between each other along the array circumference that are in communication with the interior volume of the gantry 20. Each detector 30 is of known construction, with a scintillation detector crystal 31 coupled to a detector enclosure 34 that includes light pipes and photomultiplier tubes and/or charge coupled devices for converting detector light scintillations into electrical signals, for further processing by a respective detector electronics assembly (DEA) 36 that is associated with each detector 30. DEAs 36 and other components within the gantry 20 generate heat during scanner 10 operation. Heat generated by gantry components 20 within the gantry enclosure is transferred to and absorbed by heat exchanger ring 40. Water or other coolant circulating within the heat exchanger ring 40 transfers heat away from the gantry 20. Generally the gantry 20 enclosure is sealed from the ambient environment in the patient scanning room, in order to avoid light pollution and to isolate patients from the scanner 10 apparatus. Therefore the coolant ring 40 is used as the heat transfer mechanism, rather than by direct venting to the ambient atmosphere.

Figure 4:
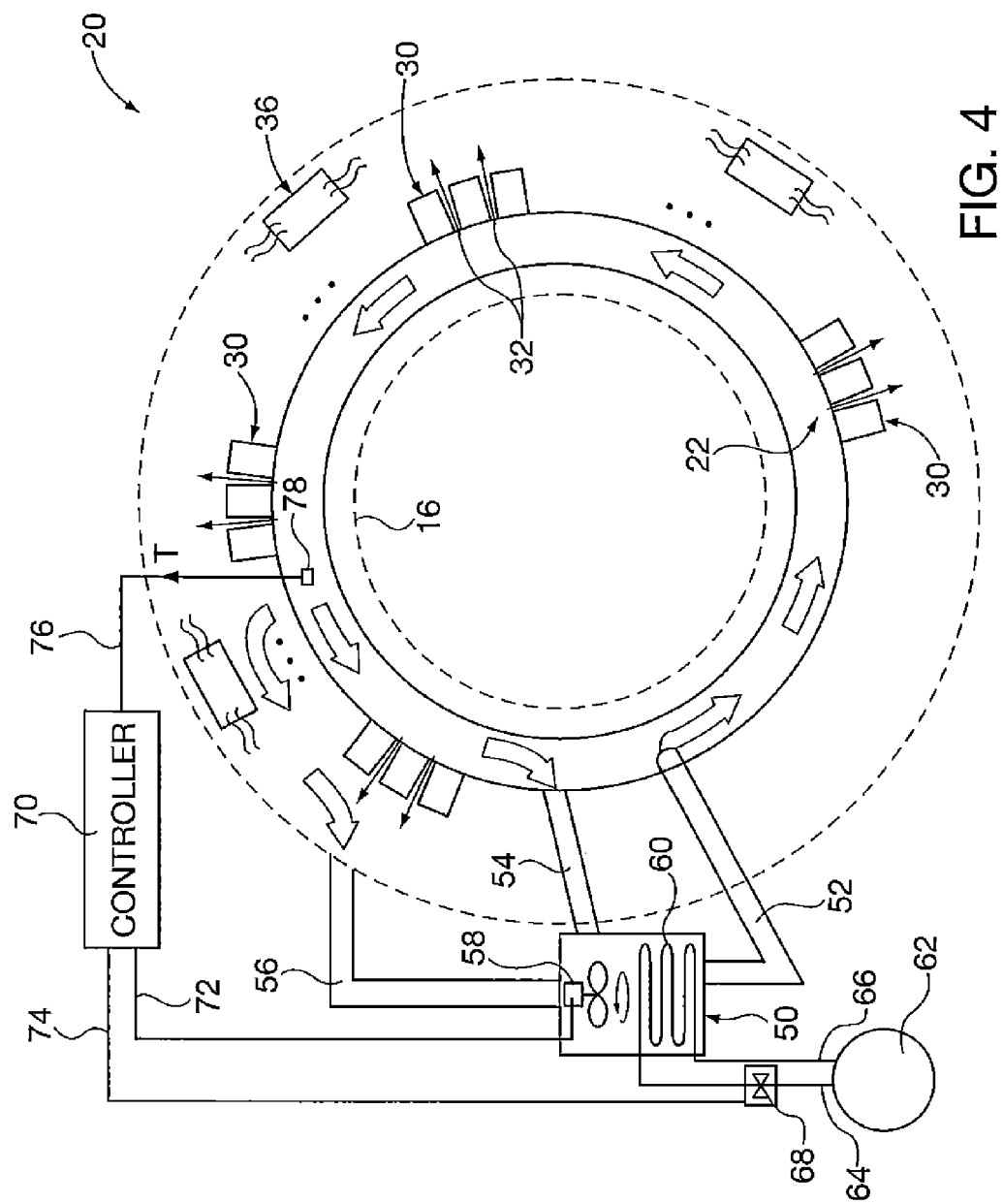
FIG. 4 is an elevational schematic view of a detector crystal cooling embodiment of the present invention.

As shown schematically in FIGS. 4 and 5, the transaxial space 22 forms a cooling duct through which is directed forced cooling gas, such as air, by a cooling system 50, by way of cooling duct intake air duct 52. Cooling air is forced to circulate within the cooling duct transaxial space 22, passing over detector crystals 31 in the detector 30 array, and returning to the cooling system by cooling duct outlet air duct 54. Air flow is also directed radially outwardly through the gaps 32 formed between detectors 30 in the array. The radial airflow additionally benefits detector crystal temperature stabilization by forming a circumferential thermal isolation barrier between the crystals 31 and heat generated by the detector electronics assemblies 36. Hot air in the outer radial periphery of the gantry 20 enclosure advantageously may be routed to the cooling system 50 by way of gantry outlet duct 56, as was air from cooling duct outlet 54. Forced airflow cooling air is circulated by motorized fan 58, where it transfers heat to heat exchanger 60 that contains a circulating fluid from a coolant source 62 (e.g., a fluid to fluid coolant heat exchanger) by way of coolant inlet 64 and coolant outlet 66. Coolant flow rate optionally may be regulated by a valve 68. The valve 68 may be a manually operated valve or a remote actuated valve under control of a known controller 70. In FIG. 4 both the fan 58 and the valve 68 receive actuation signals from controller 70 by way of respective communication pathways 72, 74. The controller has a temperature sensing input pathway 76 coupled to temperature sensor 78 that is in communication with the cooling duct transaxial space 22. The controller 70 regulates cooling air flow rate and/or temperature by selectively operating the fan 58 and/or valve 68 in response to temperature information received from the temperature sensor 78.

Figure 6:
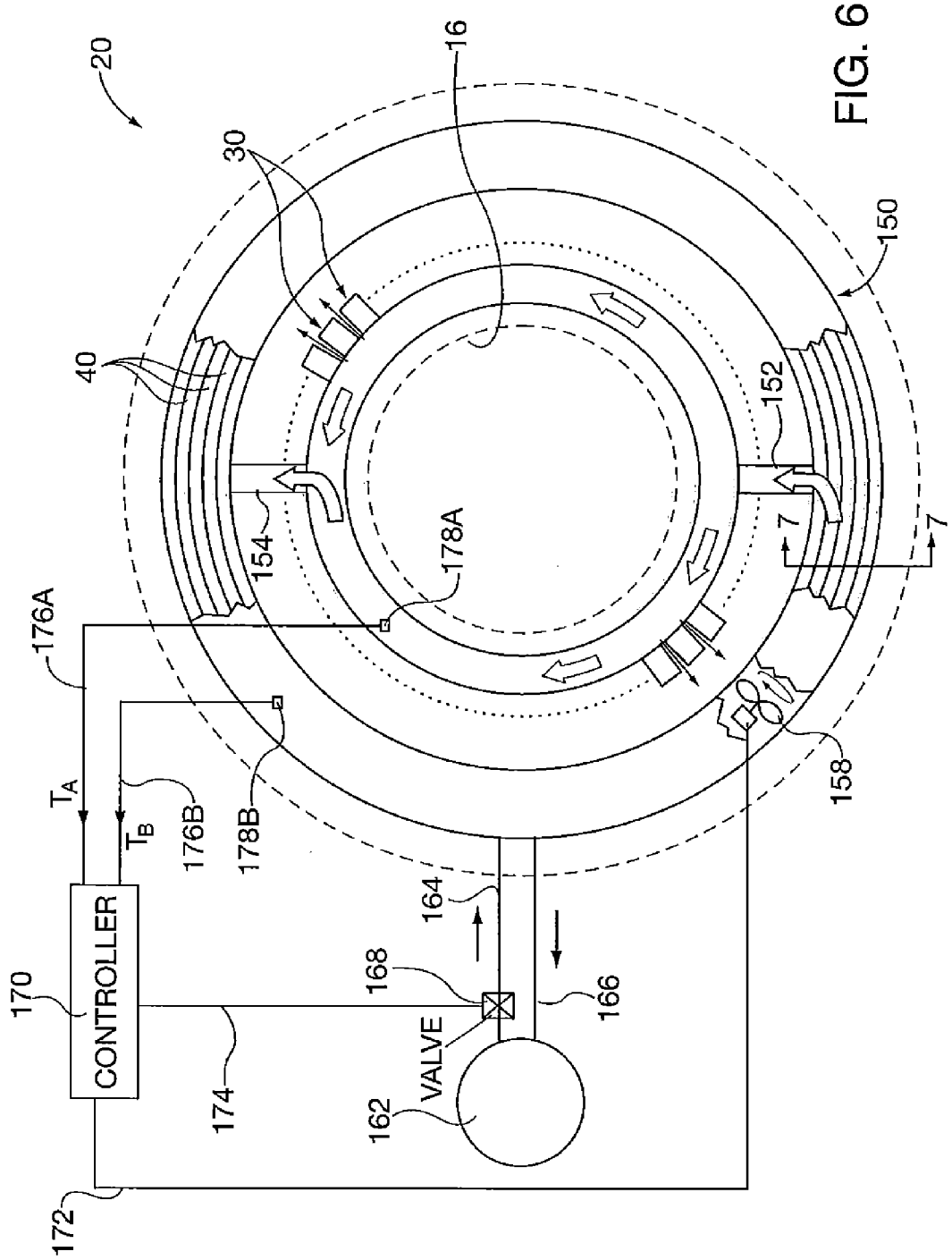
FIG. 6 is an elevational schematic view of another detector crystal cooling embodiment of the present invention.
Figure 7:
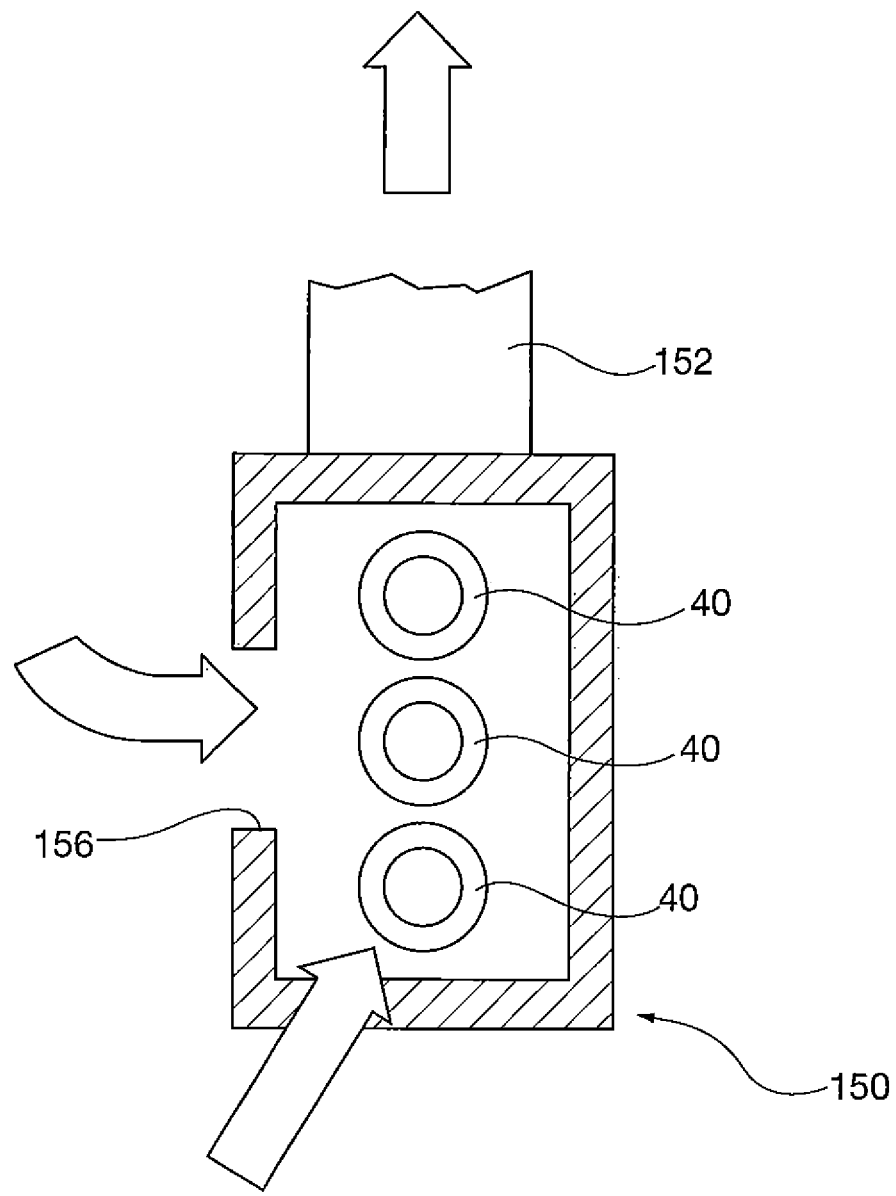
FIG. 7 is a cross-sectional elevational view taken along 7-7 of FIG. 6.

FIGS. 6 and 7 show schematically another embodiment of the detector cooling system of the present invention wherein the cooling pipes 40 within the gantry function as the cooling air heat exchanger that is coupled to the coolant external source 162 by coolant inlet 164 and outlet 166. An annular cooling pipe enclosure 150 envelops cooling pipes 40 and is in direct fluid communication with the transaxial space cooling duct 22 by way of inlet air duct 152. Cooling air flows circumferentially within cooling duct 22 and returns to the cooling pipe enclosure 150 by way of outlet air duct 154. As in the prior embodiment of FIGS. 4 and 5, cooling air is also directed radially outwardly in the gaps 32 between detectors 30, forming an isolation layer between the detector crystals 31 and the heat emitting gantry components, such as the DEAs. Warm air in the gantry 20 returns to the cooling pipe enclosure 150 through outlets 156 formed in its periphery. The warm air entering the enclosure 150 is re-cooled and recycled through the cooling duct 22.

Air cooling and circulation in the embodiment of FIGS. 6 and 7 are regulated as in the embodiment of FIGS. 4 and 5. Motorized fan 158 is in fluid communication with the enclosure 150 and cooling duct 22, causing cooling air circulation therein. Coolant flow rate optionally may be regulated by a valve 168. The valve 168 may be a manually operated valve or a remote actuated valve under control of a known controller 170. In FIG. 6 both the fan 158 and the valve 168 receive actuation signals from controller 170 by way of respective communication pathways 172, 174. The controller has two temperature sensing input pathways 176A and 176B coupled to respective temperature sensors 178A in communication with the cooling duct transaxial space 22, and 178B that is in communication with the cooling pipe 40 enclosure 150. The controller 170 regulates cooling air flow rate and/or temperature by selectively operating the fan 158 and/or valve 168 in response to temperature information received from the temperature sensors 178A, 178B. The controller 170 may be coupled to fewer or more temperature sensors than shown in the FIG. 6 embodiment. While the exemplary embodiments show use of a controller 70, 170 to regulate heat exchanger coolant temperature and cooling air fluid flow rates, the present invention can be practiced without use of a controller. For example coolant flow rate can be manually set through use of a manually actuated valve 68 or 168, or a permanently regulated flow restrictor, such as an orifice. Similarly, the forced cooling air flow motorized fan circulation rate can be manually set, or the motor powering the fan can be operated at a fixed speed.

Embodiments of the present invention circulate cooling air directly in contact with detector crystals 31 within the cooling duct transaxial space 22, and thereby enabling localized temperature regulation in the spatial volume proximal the crystals. Thus detector crystals 31 can be located in a stable temperature environment that is optimized for higher intensity scintillation and greater detector 30 sensitivity. By directing cooling air radially away from the cooling duct transaxial space 22 through the gaps 32 between detectors 30 the detector crystals 31 are thermally isolated from other heat generating components within the gantry 20. Thus energy necessary to power the coolant source 62, 162 and the air circulation fan 58, 158 is reduced compared to known gantry cooling systems that attempt to cool the entire gantry interior by convective and radiant heat transfer. While the forced cooling gas flow (e.g., air) in the embodiments of FIGS. 4-7 is performed by powered cooling fans 58, 158, a powered pressurizing pump (with or without a storage bladder or other reservoir) can be substituted for the powered fan. The cooling gas flow between the detector crystals 31 and the patient does not interfere with detector 30 sensitivity and in fact enhances detector sensitivity and stability.

Although various embodiments which incorporate the teachings of the present invention have been shown and described in detail herein, those skilled in the art can readily devise many other varied embodiments that still incorporate these teachings. For example, detector crystal material other than LSO may be utilized in the PET scanner, and the cooling system is configured to maintain a stable operating temperature suitable for those crystals. Similarly, as noted above, forced cooling gas flow over the crystals can be accomplished with a pressurizing pump rather than with a powered fan.

What is claimed is:

1. A positron emission tomography (PET) scanner apparatus comprising:
   a gantry having therein:
      a cover defining a patient scanning field within the gantry;
      a plurality of detector enclosures, each having a detector crystal facing the patient scanning field;
      a cooling duct bounded by the cover and the detector crystals; and
      a cooling system coupled to the cooling duct, for providing a source of forced cooling gas flow into the cooling duct,
      wherein spatial gaps are defined between detector enclosures, and cooling gas flows within the gaps radially away from the detector crystals.

2. The apparatus of claim 1, wherein the cooling system is in direct communication with the cooling duct.

3. The apparatus of claim 1, wherein at least a part of the cooling system is in the gantry.

4. The apparatus of claim 3, wherein at least part of the cooling system is incorporated within the cooling duct.

5. The apparatus of claim 1, wherein the cooling system is external the gantry.

6. The apparatus of claim 1, wherein the gantry and cooling system are a sealed system that isolates the cooling gas from ambient air within the patient scanning field.

7. The apparatus of claim 1, wherein the cooling system further comprises a heat exchanger having cooling tubes through which flow a cooling medium, and the cooling gas is air that is circulated over an exterior surface of the cooling tubes with a fan.

8. The apparatus of claim 1, further comprising:
   at least one temperature sensor in communication with the cooling duct for sensing temperature of the cooling gas; and
   a controller operatively coupled to the temperature sensor and the cooling system, for causing the cooling system to vary temperature of the cooling gas.

9. A positron emission tomography (PET) scanner apparatus comprising:
   a annular gantry having therein:
      a cover defining a patient scanning field within an inner radial circumference of the gantry;
      an array of a plurality of detector enclosures, each respective detector enclosure having a detector crystal facing the patient scanning field;
      a pair of opposed spaced axial shields axially bounding the detector enclosure array;
      an annular cooling duct bounded by the cover, the pair of axial shields and the detector crystals; and
      a cooling system directly coupled to the cooling duct, for providing a source of forced cooling gas flow into the cooling duct,
      wherein spatial gaps are defined between detector enclosures, and cooling gas flows within the gaps radially away from the detector crystals.

10. The apparatus of claim 9, wherein the cooling system further comprises a heat exchanger having cooling tubes within the gantry through which flow a cooling medium, and the cooling gas is air that is circulated over an exterior surface of the cooling tubes with a fan.

11. The apparatus of claim 9, further comprising:
    at least one temperature sensor in communication with the cooling duct for sensing temperature of the cooling gas; and
    a controller operatively coupled to the temperature sensor and the cooling system, for causing the cooling system to vary temperature of the cooling gas.

12. In a positron emission tomography (PET) scanner apparatus having:
    a gantry having therein:
       a cover defining a patient scanning field within the gantry;
       a plurality of detector enclosures, each having a detector crystal facing the patient scanning field;
       a cooling duct bounded by the cover and the detector crystals;

a method for cooling detector crystals, comprising:
- coupling a cooling system capable of generating a forced cooling gas flow to the cooling duct; and
- directing forced cooling gas flow into the cooling duct with the cooling system,
  - wherein spatial gaps are defined between detector enclosures, and cooling gas flows within the gaps radially away from the detector crystals.

13. The method of claim 12, wherein detector crystal comprises lutetinium oxy-orthosilicate (LSO) and the detector crystal temperature is maintained below 81° F. (27° C.) with the cooling system.

14. The method of claim 12, wherein the cooling system has a heat exchanger having cooling tubes within the gantry through which flow a cooling medium, and the cooling gas is air that is circulated over an exterior surface of the cooling tubes with a fan, the method further comprising regulating detector crystal temperature selected from the group consisting of varying cooling air temperature with the heat exchanger or cooling air flow rate with the fan.

15. The method of claim 12, wherein the scanner apparatus also has:
- at least one temperature sensor in communication with the cooling duct for sensing temperature of the cooling gas; and
- a controller operatively coupled to the temperature sensor and the cooling system, the controller capable of causing the cooling system to vary temperature of the cooling gas; the method further comprising:
  - varying temperature of the cooling gas in the cooling duct with the controller in response to temperature sensed by the temperature sensor.

16. The method of claim 15, wherein detector crystal comprises lutetinium oxy-orthosilicate (LSO) and the detector crystal temperature is maintained below 81° F. (27° C.) with the cooling system.

17. The method of claim 15, wherein the cooling system has a heat exchanger having cooling tubes within the gantry through which flow a cooling medium, and the cooling gas is air that is circulated over an exterior surface of the cooling tubes with a fan, the method further comprising regulating detector crystal temperature selected from the group consisting of varying cooling air temperature with the heat exchanger or cooling air flow rate with the fan.

* * * * *